(12) United States Patent
MacAdam et al.

(10) Patent No.: US 8,845,558 B2
(45) Date of Patent: Sep. 30, 2014

(54) METHODS AND APPARATUS FOR CONFIGURING AN ABLATION SOURCE OF A CATHETER

(75) Inventors: David MacAdam, Millbury, MA (US); Timothy Collins, Mendham, NJ (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1680 days.

(21) Appl. No.: 11/885,214

(22) PCT Filed: Feb. 28, 2006

(86) PCT No.: PCT/US2006/006900
§ 371 (c)(1),
(2), (4) Date: Aug. 20, 2009

(87) PCT Pub. No.: WO2006/093895
PCT Pub. Date: Sep. 8, 2006

(65) Prior Publication Data
US 2009/0306549 A1    Dec. 10, 2009

Related U.S. Application Data

(60) Provisional application No. 60/657,003, filed on Feb. 28, 2005.

(51) Int. Cl.
*A61N 7/00* (2006.01)
*A61N 7/02* (2006.01)

(52) U.S. Cl.
USPC ............. 601/2; 601/3; 600/437; 600/459; 600/462; 600/466

(58) Field of Classification Search
None
See application file for complete search history.

(56) References Cited

U.S. PATENT DOCUMENTS

| | | | |
|---|---|---|---|
| 5,125,410 A | 6/1992 | Misono et al. | |
| 5,383,460 A | 1/1995 | Jang et al. | |
| 6,117,101 A | 9/2000 | Diederich et al. | |
| 6,176,842 B1 * | 1/2001 | Tachibana et al. | 604/22 |
| 6,361,531 B1 * | 3/2002 | Hissong | 606/27 |
| 2003/0229286 A1 | 12/2003 | Lenker | |
| 2004/0077976 A1 * | 4/2004 | Wilson | 601/2 |
| 2005/0261585 A1 * | 11/2005 | Makin et al. | 600/439 |

FOREIGN PATENT DOCUMENTS

WO    9956627 A1    11/1999

* cited by examiner

*Primary Examiner* — Long V. Le
*Assistant Examiner* — Bradley Impink
(74) *Attorney, Agent, or Firm* — Seager, Tufte & Wickhem LLC

(57) ABSTRACT

Embodiments of the invention relate to a catheter having an ultrasound energy emitting region that is both rotatable about and slidable along the shaft of the catheter. One embodiment is directed to a catheter comprising an ultrasound transducer coupled to the shaft, and at least one actuator coupled to the handle and the ultrasound transducer that is adapted to move the ultrasound transducer both longitudinally along the shaft and circumferentially about the shaft. Another embodiment of the invention is directed to a catheter comprising an ultrasound transducer coupled to the shaft, and at least one actuator that is adapted to move the sheath both longitudinally along the shaft and circumferentially about the shaft to orient a window of the sheath in a desired position.

10 Claims, 8 Drawing Sheets

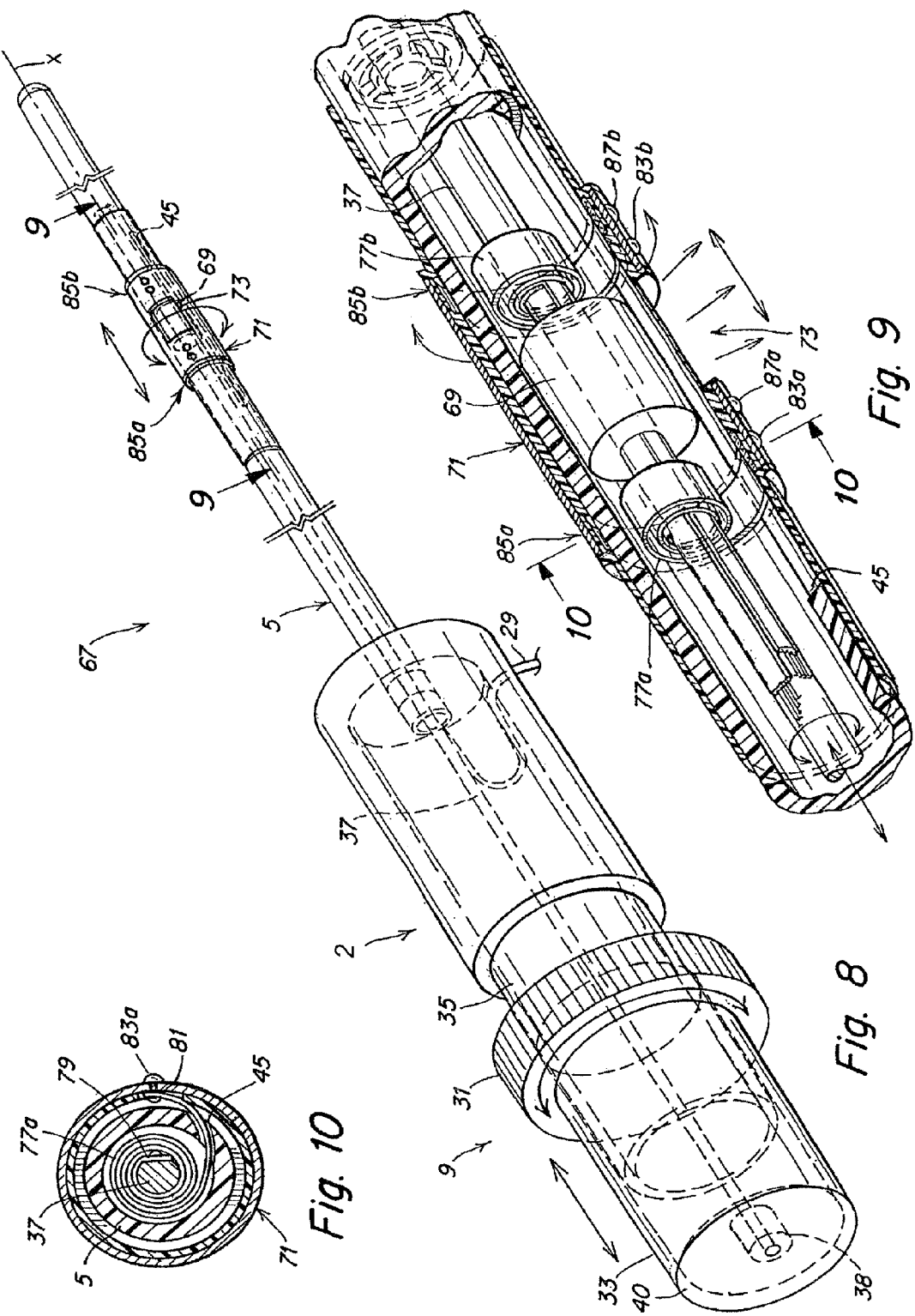

METHODS AND APPARATUS FOR CONFIGURING AN ABLATION SOURCE OF A CATHETER

CROSS-REFERENCE TO RELATED APPLICATIONS

This application claims the benefit, under 35 U.S.C. §119 (e), of the filing date of U.S. provisional application Ser. No. 60/657,003 entitled "Rotatable Catheter Assembly," filed Feb. 28, 2005, which is hereby incorporated herein by reference in its entirety.

FIELD OF INVENTION

The invention relates generally to methods and apparatus for ablating tissue using an ablation energy source, such as an ultrasound transducer.

BACKGROUND OF INVENTION

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrhythmogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrhythmogenic focus. Ablation is carried out by applying energy to the catheter electrodes. The ablation energy can be, for example, radiofrequency (RF), direct current (DC), ultrasound, microwave, or laser radiation.

SUMMARY OF INVENTION

One embodiment of the invention is directed to a catheter comprising a handle, a shaft coupled to the handle, an ultrasound transducer coupled to the shaft, and at least one actuator coupled to the handle and the ultrasound transducer. The at least one actuator is adapted to move the ultrasound transducer both longitudinally along the shaft and circumferentially about the shaft.

Another embodiment of the invention is directed to a catheter comprising, a handle, a shaft coupled to the handle, an ultrasound transducer coupled to the shaft, a sheath disposed at least partially about the ultrasound assembly, wherein the sheath comprises a window having a greater transmissivity to ultrasound energy than the sheath, and at least one actuator coupled to the handle and the sheath. The at least one actuator is adapted to move the sheath both longitudinally along the shaft and circumferentially about the shaft to orient the window of the sheath in a desired position.

A further embodiment of the invention is directed to a catheter comprising a handle, a shaft coupled to the handle, the shaft having a central longitudinal axis, and an ultrasound assembly, coupled to the shaft, comprising an ultrasound transducer disposed between first and second end portions. A radial distance from an outer surface of each of the first and second end portions to the central longitudinal axis of the catheter is greater than a radial distance of an outer surface of the ultrasound transducer to the longitudinal axis of the catheter.

Another embodiment of the invention is directed to a system comprising a controller comprising an ultrasound generator and a catheter. The catheter comprises a handle, a shaft coupled to the handle, the shaft having a central longitudinal axis, and an ultrasound assembly, coupled to the shaft. The ultrasound assembly comprises an ultrasound transducer disposed between first and second end portions. A radial distance from an outer surface of each of the first and second end portions to the central longitudinal axis of the catheter is greater than a radial distance of an outer surface of the ultrasound transducer to the longitudinal axis of the catheter.

A further embodiment of the invention is directed to a method of using a catheter to treat tissue in the heart, the catheter comprising an ultrasound transducer coupled to a shaft of the catheter and a sheath disposed about the ultrasound transducer. The method comprises within the heart, configuring the catheter such that a desired portion of the ultrasound transducer is not obscured by the sheath and forming a lesion in the tissue using ablation energy emitted from the portion of the ultrasound transducer not obscured by the sheath.

BRIEF DESCRIPTION OF DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings:

FIGS. 1 and 3-5 illustrate a catheter according to an embodiment of the invention;

FIGS. 8-10 illustrate a catheter according to another embodiment of the invention;

DETAILED DESCRIPTION

To effectively treat a cardiac arrhythmia, a lesion providing a sufficient conduction block should be created in the heart in order to disable or disrupt the propagation of an errant impulse. To form a sufficient lesion, it is desirable to orient an ablation energy source so that it is facing the desired area of tissue where the lesion is to be formed. Because of the motion of the heart and the difficulty associated with maneuvering a catheter within the heart, it can be difficult to position a directed ablation energy source (e.g., an ultrasound energy source) so that it is facing the desired area.

In view of the foregoing, an improved catheter is disclosed herein that may be configured such that an ablation energy emitting region is facing a desired area for ablation. Specifically, the ablation energy emitting region may be slidable along a central longitudinal axis of the catheter and/or rotatable with respect to the axis of the catheter. In embodiments described herein, the ablation energy emitting region may comprise a slidable and/or rotatable transducer coupled to a shaft or a region of a transducer that is exposed through a window in a slidable and/or rotatable sheath.

Figure 1:
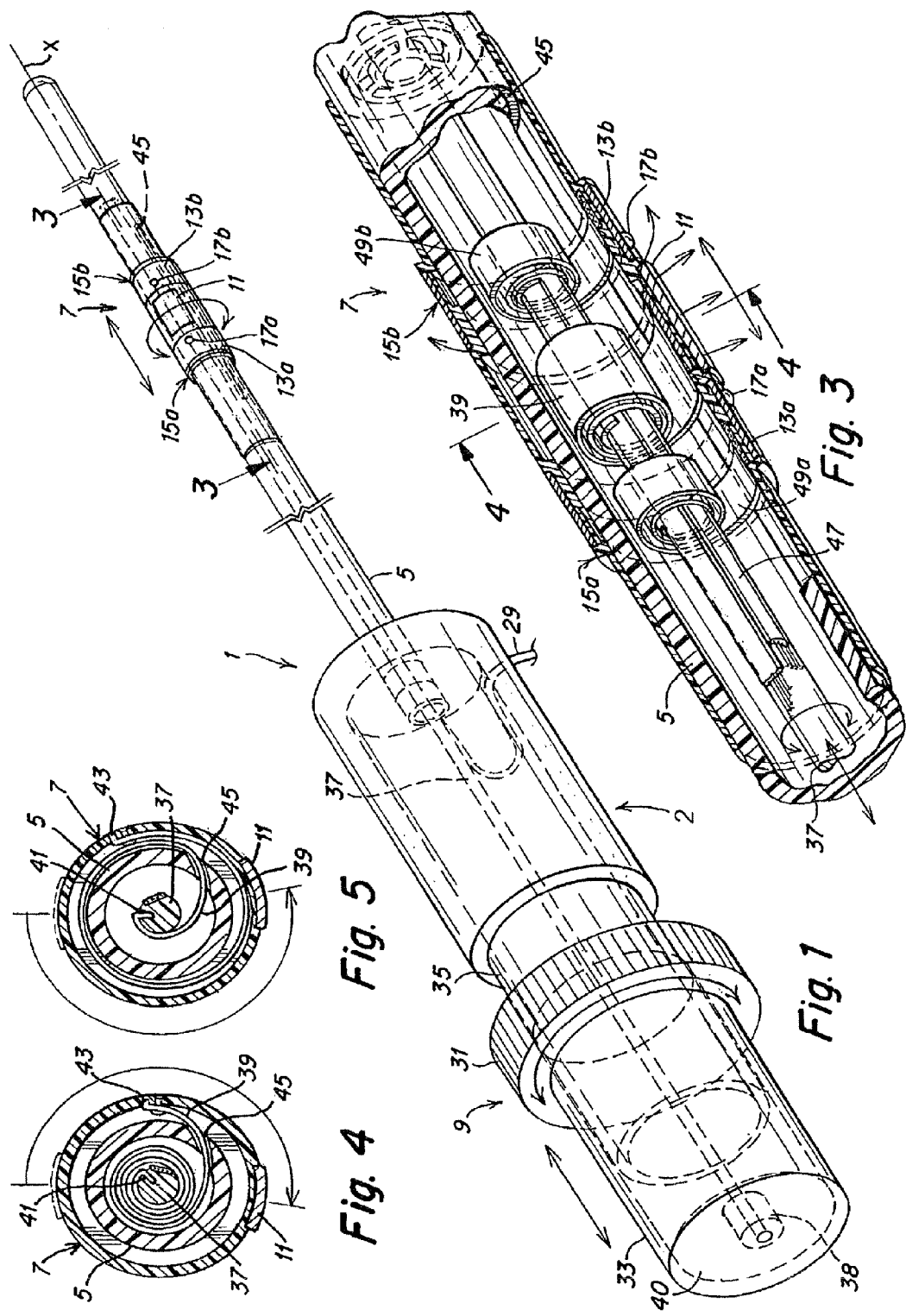

FIG. 1 shows a first embodiment of a catheter having a configurable ablation energy emitting region. Catheter 1 comprises a handle 2 coupled to a shaft 5 on which an ultrasound assembly 7 is disposed. The ultrasound assembly 7 is both slidable along and rotatable about a central longitudinal axis x of the catheter. The handle comprises an actuator 9 to control longitudinal and rotational movement of the ultrasound assembly 7.

The ultrasound assembly 7 comprises an ultrasound transducer 11, which generates ablation energy in the form of ultrasonic pressure waves. The ultrasound transducer 11 may comprise a piezoceramic or piezoelectric crystalline material. As an alternating current is applied to the ultrasound transducer 11, the transducer vibrates across its thickness and causes ultrasonic energy to radiate outwardly therefrom. Ultrasonic energy is sound having a frequency above the range of human hearing, or above approximately 20 kHz. This ultrasonic energy causes heating and ablation of the tissue. According to one exemplary implementation, the ultrasound transducer 11 is approximately 4 mm in length, but other lengths may be preferred according to the lesion to be formed. The thickness of the ultrasound transducer may be selected based on a desired operating frequency. For example, the transducer may be operated at a frequency between 5 MHz and 20 MHz, and may have a thickness approximately equal to half the wavelength of the output signal. The frequency of operation of the ultrasound transducer 11 may be varied based on desired dimensions of the lesion and other factors.

The ultrasound assembly further comprises first and second electrodes 13a, 13b disposed on first and second end portions 15a, 15b of the ultrasound assembly 7. One or both of the electrodes 13a, 13b may be used for sensing signals from the heart in either bipolar or unipolar mode. Alternatively or additionally, one or both of the electrodes 13a, 13b may be used to transmit pacing signals to the heart. In one example, one electrode is used to generate pacing signals and the other electrode is used to sense signals (e.g., the pacing signals). According to another example, the electrodes 13a, 13b may be used to deliver ablation energy (e.g., radiofrequency (RF) or ultrasound ablation energy) to the heart. It should be appreciated that the electrodes 13a, 13b are not required, and that the first end portion 15a and/or second end portion 15b may instead comprise a non-metallic support structure or other non-electrode structure. Further, electrodes (e.g., pacing electrodes, ablation electrodes, mapping electrodes, and/or reference electrodes) may be included elsewhere on the catheter, for example on the catheter shaft 5.

The first and second end portions 15a, 15b also respectively comprise first and second temperature sensors 17a, 17b disposed adjacent the ultrasound transducer 11. The first and second end portions 15a, 15b are rotatable along with the ultrasound transducer 11 such that the temperature sensors 17a, 17b remain co-linear with the ultrasound transducer 11 as it is rotated. The temperature sensors 17a, 17b may detect a temperature of the tissue during ablation, for example to ensure that the tissue does not overheat and/or char. The temperature sensors 17a, 17b may be implemented as thermocouples, thermistors, infrared or optical sensors, or other suitable sensors. To indicate the location and orientation of the ultrasound transducer when the catheter is viewed during fluoroscopy or other x-ray or imaging procedures, the temperature sensors 17a, 17b may comprise a radio-opaque material. Alternatively or additionally, independent radio-opaque markers may be used. It should be appreciated that temperature sensors 17a, 17b and radio-opaque markers are optional features that need not be included on ultrasound assembly 7.

Figure 2:
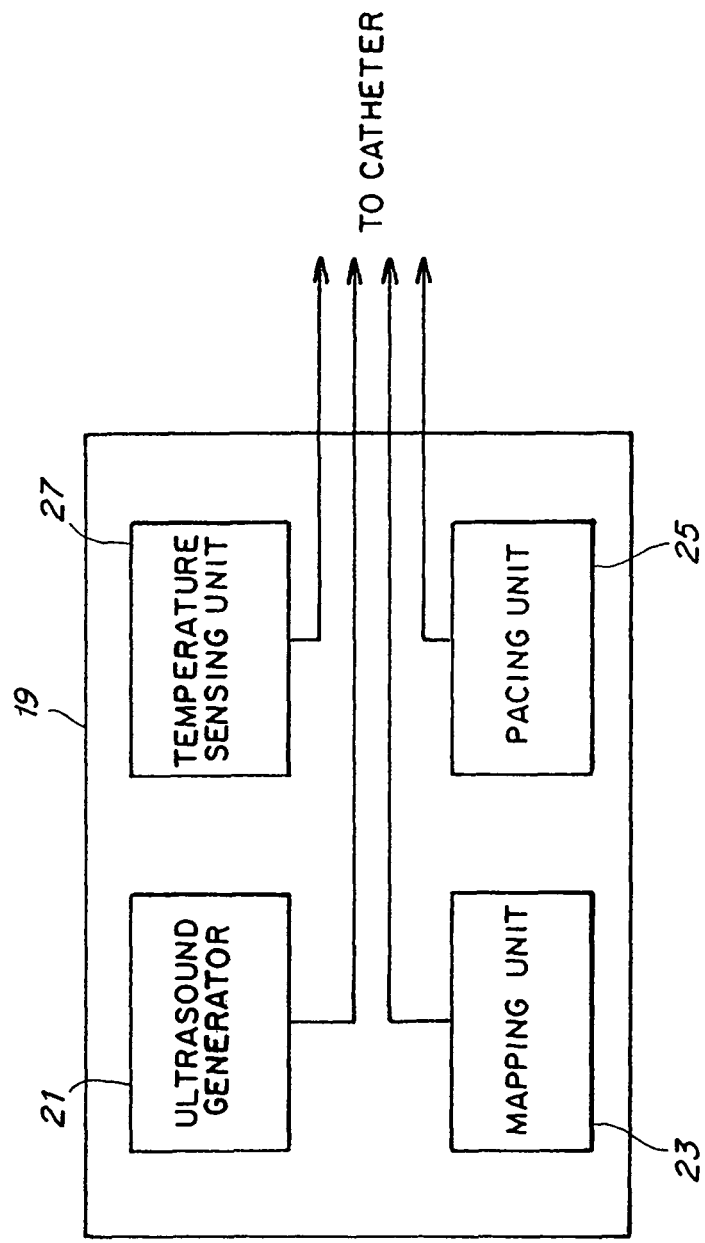
FIG. 2 illustrates a controller according to an embodiment of the invention.

A controller may be coupled to the catheter 1, and the other catheters described herein, to provide ablation, mapping, pacing, and/or temperature sensing capabilities. As shown in FIG. 2, the controller 19 comprises an ultrasound generator 21, a mapping unit 23, a pacing unit 25, and/or a temperature sensing unit 27. The ultrasound generator 21 provides electrical energy, e.g., in the form of an alternating current, to the ultrasound transducer. The ultrasound generator may also be used as a receiver to check the distance to the targeted ablation site, as well as to monitor the acoustic impedance changes during ablation. This assists in guiding the assembly to the targeted ablation site. The mapping unit 23 processes signals that may be received from electrodes (e.g., electrodes 13a, 13b) on the catheter. The pacing unit 25 generates pacing signals that may be transmitted to electrodes (e.g., electrodes 13a, 13b) on the catheter. The temperature sensing unit 27 processes temperature signals detected by temperature sensors 17a, 17b. Each of the ultrasound generator 21, mapping unit 23, pacing unit 25, and temperature sensing unit 27 may be electrically coupled to a cable 29 (FIG. 1) of the catheter 1. Intermediate connectors may be included on the cable 29 and controller 19 so that the catheter 1 may be easily connectable and detachable from the controller 19.

Referring again to FIG. 1, the handle 2 comprises an actuator 9 to control longitudinal and rotational movement of the ultrasound assembly 7. The actuator 9 comprises a wheel 31 disposed on a cylindrical sleeve 33. A cylindrical inner member 35 of the handle 2 is received within the sleeve. The cylindrical sleeve 33 is slidable over and rotatable about the cylindrical inner member 35, for example by manipulating the wheel 31. This longitudinal and/or rotational movement of the sleeve 33 is translated to a mandrel 37 coupled thereto. The mandrel 37 is fixedly attached to the sleeve via an anchor 38 on an end 40 of the sleeve 33 and runs along the central longitudinal axis of the sleeve. The mandrel 37 travels through the shaft 5 from the handle 2 and is coupled to the ultrasound assembly 7 to rotate and/or slide the assembly along the shaft 5. The mandrel is preferable formed of a material (e.g., Nitinol or stainless steel) of sufficient stiffness so as to be rotatable and movable under compression. It should be appreciated that although a single actuator 9 is shown and described as controlling both rotational and longitudinal movement of the ultrasound assembly 7, separate actuators could alternatively be used.

Other user interface features may be included on the handle 2 if desired. For example, a locking mechanism may be provided to temporarily stop or lock the rotational and/or sliding movement of the actuator 9, and hence the mandrel 37. In addition, a switch may be included on the handle 2 to cause the controller to read and/or display a temperature measured by one or more of temperature sensors 17a and 17b. The handle may also display the temperature reading or provide other visual or sensory information to the user. For example, an indication of the degree of rotation of the actuator 9 may be provided, which corresponds to the radial location of the ultrasound transducer. This indication may be visual (e.g., using numbers or other markers) or tactile (e.g., a varying degree of friction). Similarly, an indication of the degree of longitudinal extension of the actuator 9 may be provided, which corresponds to a longitudinal location of the ultrasound transducer.

The mechanics and operation of the ultrasound assembly 7 will be described in more detail in connection with FIGS. 3-5. FIG. 3 shows a perspective cut-away view of catheter 1 between arrows 3 of FIG. 1. As shown, the ultrasound assembly 7 is coupled to the mandrel 37 via a clock spring 39. Specifically, the clock spring 39 is anchored to the mandrel 37 at an anchor 41 and to the ultrasound assembly 7 at an anchor 43, as shown in FIGS. 4-5. Because the ultrasound assembly 7 is disposed about the catheter shaft 5, the clock spring 39 travels through a slot 45 in the shaft to connect the ultrasound assembly 7 with the mandrel 37. The slot 45 runs lengthwise along the shaft to allow the clock spring 39 to slide as the ultrasound assembly 7 is moved longitudinally. Thus, the slot 45 has a length approximately equal to the length that the ultrasound assembly 7 may be slid along the catheter 1. The slot may include a skirt to reduce or prevent the entry of fluids and debris into the catheter 1. To rotate the ultrasound assembly 7, the mandrel 37 is rotated, which causes the clock spring 39 to coil or uncoil as shown in FIGS. 4 and 5, described further below.

FIGS. 4 and 5 show cross-sectional views of the catheter 1 at line 4-4 of FIG. 3. FIG. 4 shows the clock spring 39 fully retracted within the shaft 5, whereas FIG. 5 shows the clock spring 39 fully extended from the shaft 5. The catheter 1 can be reconfigured between the arrangement of FIG. 4 and the arrangement of FIG. 5 by rotating the mandrel 37 and ultrasound assembly 7 counterclockwise, and between the arrangement of FIG. 5 and the arrangement of FIG. 4 by rotating the mandrel 37 and ultrasound assembly 7 clockwise. In the example shown, the ultrasound assembly 7 is rotatable bidirectionally by an angle of greater than 360°. The clock spring 39 may be formed of a metallic material or another material of sufficient stiffness to be moveable under compression to cause rotation of the ultrasound assembly 7.

To electrically connect the ultrasound transducer 11, electrodes 13a, 13b, and temperature sensors 17a, 17b to the controller 19 (FIG. 2), wires 47 are provided that enter the catheter via the cable 29 and run through the shaft 5 along the mandrel 37. In the ultrasound assembly 7, the wires 47 enter ribbon cables 49a, 49b, which are coiled about the mandrel 37. The ribbon cables 49a, 49b pass through the slot 45 and are anchored to the ultrasound assembly 7. The ribbon cables 49a, 49b are of a sufficient length so that the cables can coil and uncoil as the mandrel is rotated in the same manner as the clock spring 39. Wires of the ribbon cable are coupled to the ultrasound transducer 7, electrodes 13a, 13b, and temperature sensors 17a, 17b to provide and receive signals as described herein. However, it should be appreciated that alternative configurations are possible, and that wires may run through the shaft 5 and be attached to the ultrasound assembly 7 in other manners.

Figure 6:
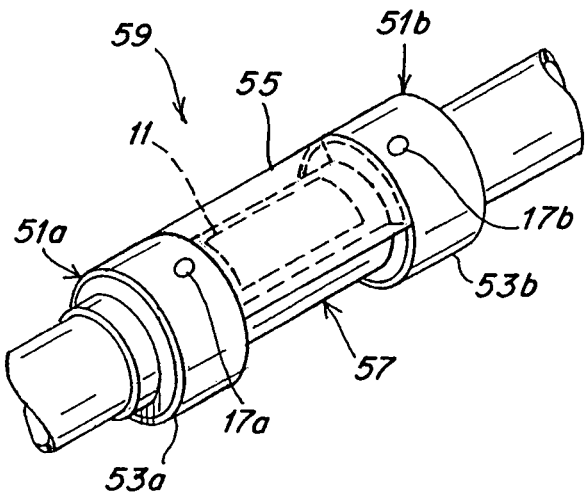
FIG. 6 illustrates an alternate configuration of the ultrasound assembly of FIGS. 1 and 3-5.
Figure 7:
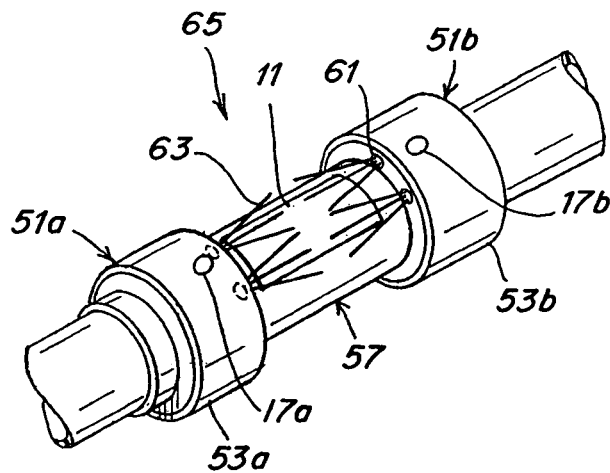
FIG. 7 illustrates another alternate configuration of the ultrasound assembly of FIGS. 1 and 3-5.

FIGS. 6-7 show alternate configurations of the ultrasound assembly described in connection with FIGS. 1 and 3-5. In particular, the ultrasound assemblies of FIGS. 6-7 comprise end portions 51a, 51b each having a larger diameter than the central portion including the ultrasound transducer 11. Thus, the surfaces of the electrodes 53a, 53b on end portions 51a, 51b are further from the central longitudinal axis of the catheter than is the surface of the ultrasound transducer 11. As a result, the distance between the ultrasound transducer 11 and adjacent tissue during an ablation procedure is offset by the end portions 51a, 51b. This offset may enhance the transmission of ultrasound energy to the tissue and the contact of the electrodes 53a, 53b with the tissue.

To improve the transmission of ultrasound energy from the ultrasound transducer 11 to the tissue, it may be desirable to include an acoustic coupling medium therebetween. In the example of FIG. 6, an acoustic coupling medium 55 is disposed on the central portion 57 of the ultrasound assembly 59 over the ultrasound transducer 11. The medium may comprise a gel material or other soft or non-rigid material that has impedance matching properties. Alternatively, the medium may comprise a contained fluid (e.g., saline within a balloon). Other acoustic coupling media are also possible. In the example of FIG. 7, irrigation ports 61 are provided in end portions 51a, 51b to direct acoustic coupling fluid 63 to the region between the ultrasound transducer 11 and the tissue. Alternatively, the irrigation ports 61 may be used to deliver cooling fluid, contrast media, drugs or other therapeutic fluids. To supply fluid to the irrigation ports 61, one or more fluid tubes may be coupled to the ultrasound assembly 65 in a manner similar to the connection arrangement for the ribbon cables 49a, 49b discussed in connection with FIG. 3.

FIGS. 8-10 show another embodiment of a catheter having a configurable ablation energy emitting region. Catheter 67 comprises a handle 3 coupled to a shaft 5 in which an ultrasound transducer 69 is disposed. A sheath 71 is disposed about an area of the shaft 5 comprising the ultrasound transducer 69. The sheath 71 and ultrasound transducer 69 are coupled together such that they are moveable together. Specifically, the sheath 71 and ultrasound transducer 69 are slidable along and rotatable about a central axis of the catheter by manipulating the handle 3 in the same manner as described in connection with FIG. 1. The sheath 71 comprises a window 73 having a greater transmissivity to ultrasound energy than the other portions of the sheath 71 such that ultrasound energy is primarily or exclusively transmitted through the window. By rotating the sheath 71 about the central axis of the catheter 67, the window 73 can be oriented to a radial position where ultrasound energy is desired. Likewise, by sliding the sheath 71 and ultrasound transducer 69 along the central axis of the catheter 67, the window 73 and ultrasound transducer 69 can be oriented to a longitudinal position where ultrasound energy is desired.

Figure 11:
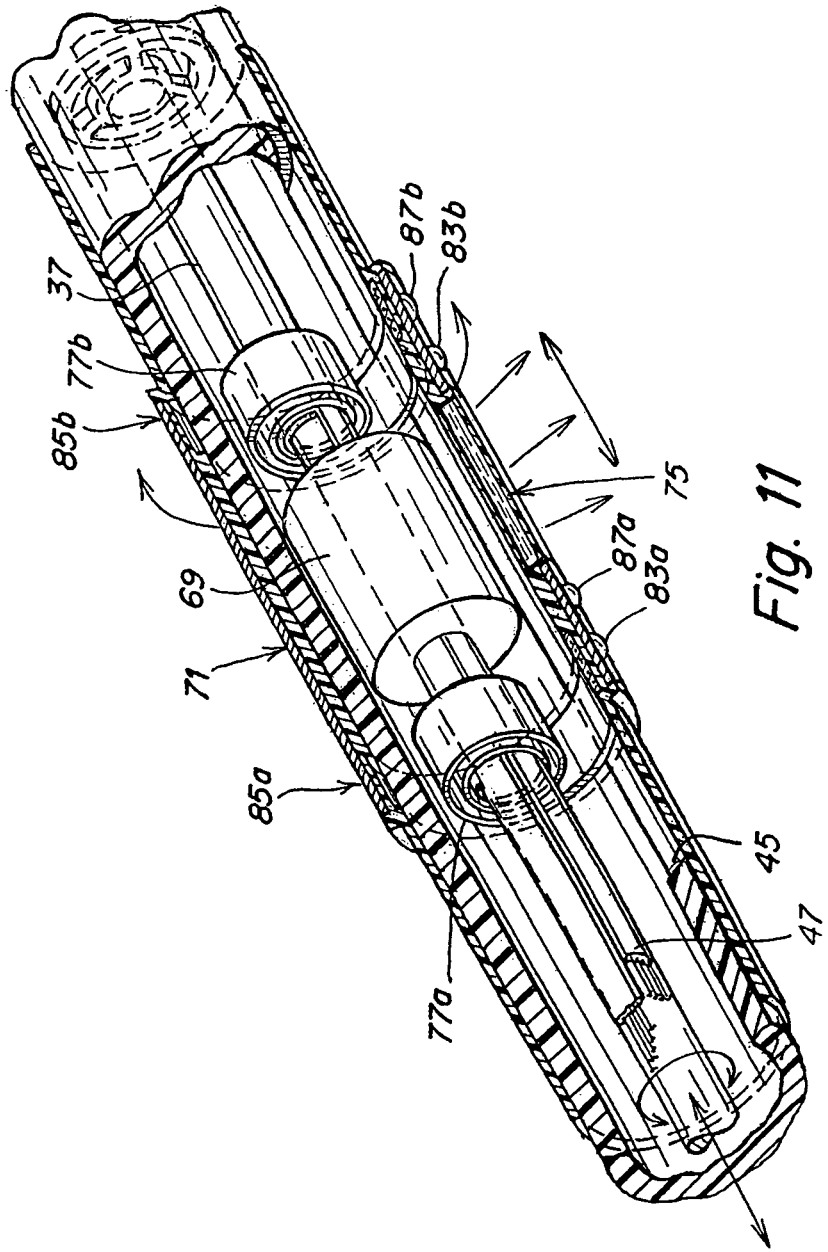
FIG. 11 illustrates an alternate configuration of the sheath of FIGS. 8-10.

Window 73 may merely comprise an opening such that ultrasonic pressure waves emitted by the ultrasound transducer 69 exit the catheter 67 without passing through any material of the catheter 67, as shown in FIG. 9. Alternatively, the window 73 may comprise a pane 75, as shown in FIG. 11. The pane 75 may be constructed of an acoustic coupling material, such as those described herein, to facilitate the transmission of ultrasound energy to the heart tissue.

The sheath 71 is slid along and rotated about the shaft 5 in a manner similar to that described for the ultrasound assembly of FIG. 1. However, in this configuration, the ribbon cables 77a, 77b that form the electrical connection between the shaft 5 and the sheath 71 also cause the sheath 71 to rotate as the mandrel 37 is rotated. Thus, the ribbon cables 77a, 77b are formed of a material of a sufficient stiffness to be moveable under compression to cause rotation of the sheath 5. FIG. 10 shows a cross-sectional view of catheter 67 at line 10-10 of FIG. 9. As shown, ribbon cable 77a is anchored to the mandrel 37 at anchor 79 and to the sheath 71 at anchor 81. The ribbon cable 77a travels through a slot 45 in the shaft to connect the sheath 71 to the mandrel 37. The slot 45 runs lengthwise along the shaft to allow the ribbon cables 77a, 77b to slide as the sheath 71 is moved longitudinally. Thus, the slot 45 has a length approximately equal to the length that the sheath 71 may be slid along the catheter 67, and may include a skirt to reduce or prevent the entry of fluids and debris into the catheter 67. The wires of ribbon cable 77b may pass under ultrasound transducer 69, along the mandrel 37, to reach a location distal to the ultrasound transducer 69.

The ultrasound transducer 69 may have similar properties to the ultrasound transducer described in connection with FIGS. 1 and 3. Further, one or more quarter-wave layers can be included on the ultrasound transducer 69, or on the ultrasound transducers of any of the embodiments described herein, to serve as acoustic impedance matching layers. It should be appreciated that the illustrated dimensions of the ultrasound transducer 69 are not intended to be limiting, and that other shapes and sizes may be used.

Similar to the ultrasound assembly of FIGS. 1 and 3, the sheath 71 comprises first and second electrodes 83a, 83b disposed on first and second end portions 85a, 85b of the sheath 71. These electrodes may have any of the properties described for the electrodes of other embodiments described herein. It should be appreciated that electrodes 83a, 83b are not required, and that the first end portion and/or second end portion 85a, 85b may instead comprise a non-metallic support structure or other non-electrode structure.

In addition, the first and second end portions 85a, 85b respectively comprise first and second temperature sensors 87a, 87b disposed adjacent the window 73. The first and second end portions 85a, 85b may be rotatable along with the window 73 such that the temperature sensors 87a, 87b remain collinear with the window 73 as it is rotated. The temperature sensors may have any of the properties described for the temperature sensors of other embodiments described herein. It should be appreciated that temperature sensors 87a, 87b are optional features that need not be included on sheath 71.

Figures 12, 13:
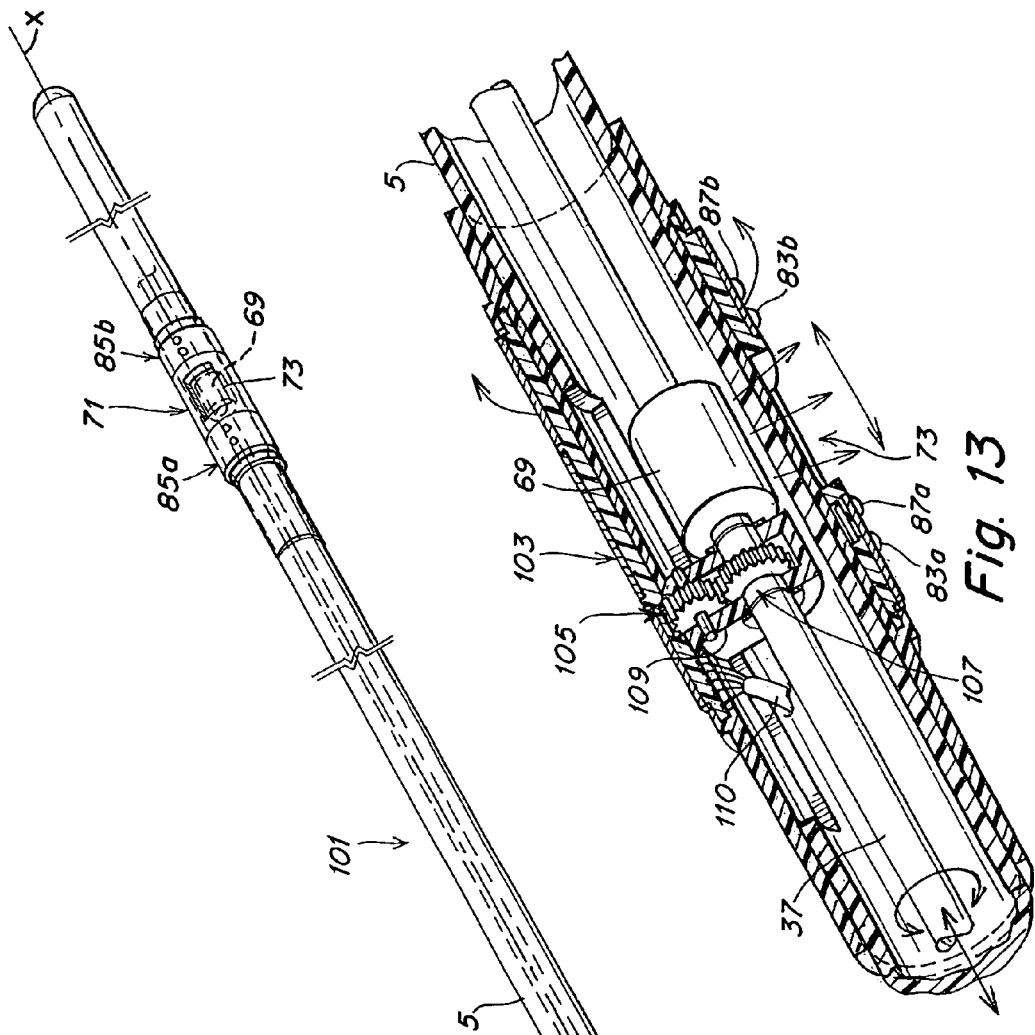
FIG. 12 illustrates an alternate configuration of the handle of FIG. 8.
FIG. 13 illustrates an alternate configuration of the mechanism for rotating and sliding the sheath of the catheter of FIG. 9.

FIG. 12 shows an alternate configuration of a handle for the catheter described in connection with FIG. 8. Catheter 101 includes a handle 89 comprising a housing 91, a knob actuator 93, and a slidable assembly 95 disposed in the housing and coupled to the knob actuator. The slidable assembly 95 comprises a gear assembly 97 that translates the rotational motion of the knob actuator 93 to rotational motion of the mandrel 37. The slidable assembly 95 slides within the housing 91 as the knob actuator 93 is slid along the slot 99, which in turn causes the mandrel 37 coupled to the slidable assembly 95 to slide within the shaft 5. It should be appreciated that the handle configuration of FIG. 12 may also be used for the catheter described in connection with FIG. 1, or other embodiments described herein.

FIG. 13 shows an alternate configuration of a mechanism for rotating and sliding the sheath of the catheter described in connection with FIG. 9. The sheath 103 is the substantially the same as the sheath 71 of FIGS. 8 and 9, but comprises a gear interface 105 for interfacing with a gear assembly 107 coupled to the mandrel 37. The gear assembly 107 translates rotational motion of the mandrel 37 to rotational motion of the sheath 103. Walls 109 of the gear interface are coupled to the sheath 103 such that as the mandrel 37 is moved longitudinally within the shaft 5, the sheath 103 moves a corresponding distance. Electrodes 83a, 83b, temperature sensors 87a, 87b, window 73, and the other features of sheath 103 may have any of the properties described in connection with the sheath 71 of FIGS. 8 and 9. A cable 109, which may be used in addition to or in place of a ribbon cable such as the ribbon cable 77a, 77b described in connection with FIG. 9, provides electrical signals to the electrodes 83a, 83b and temperature sensors 87a, 87b. A similar cable may be used to provide electrical signals to ultrasound transducer 69.

Figure 14:
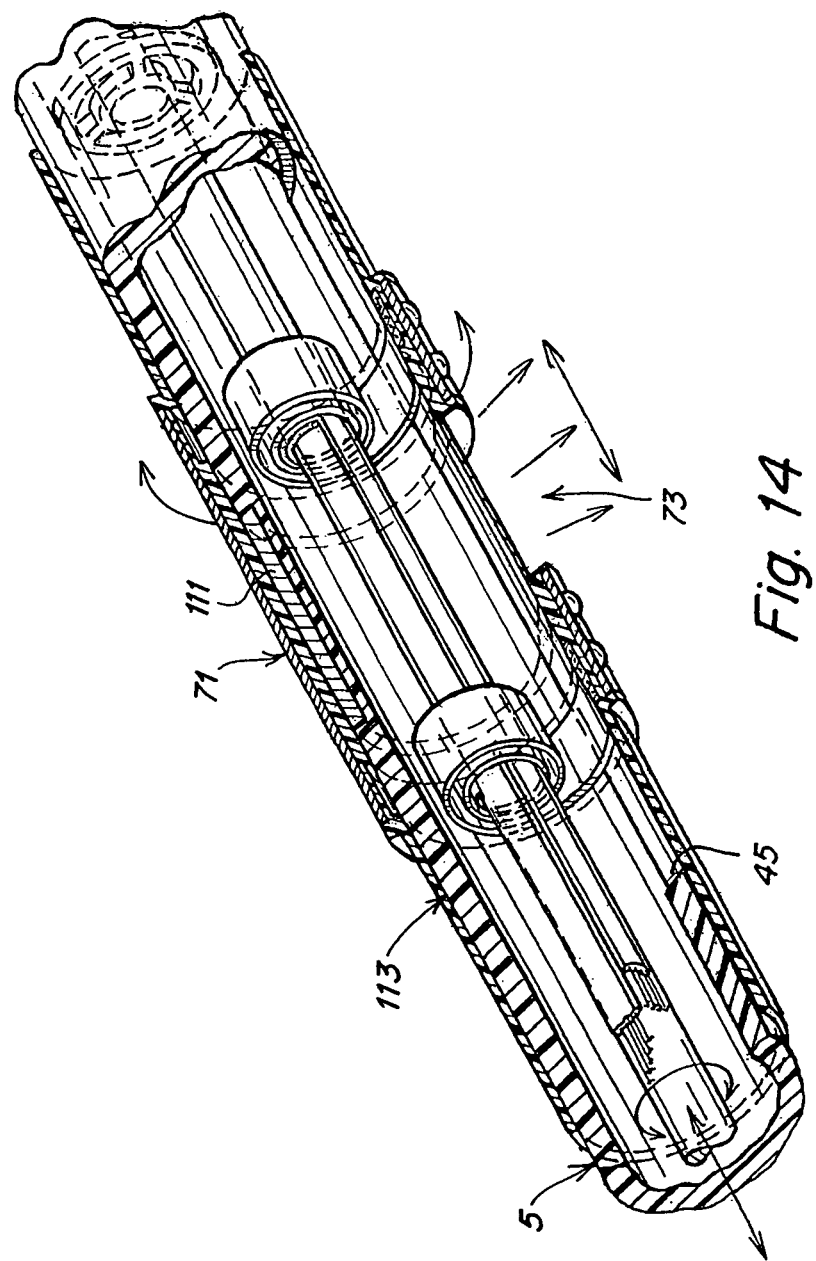
FIG. 14 illustrates a catheter according to a further embodiment of the invention.

Although the ultrasound transducer 69 of FIGS. 13 and 9 is shown and described as being within the shaft, other arrangements are possible. For example, FIG. 14 shows an embodiment that is the similar to the embodiment of FIG. 9, but includes a transducer 111 is recessed within an outer wall 113 of the shaft 5 rather than within the shaft 5. Thus, the ultrasound transducer 111 is in a fixed position with respect to the shaft. To reconfigure the ablation energy emitting region, the sheath 71 is slid along and rotated about the shaft in the same manner previously described. The ultrasound transducer 111 therefore may extend about the full rotational range of the window 73 of the sheath (e.g., 360°), except where the slot 45 in the shaft 5 is formed. Further, the ultrasound transducer 111 may extend the full longitudinal range of the window 73 of the sheath (e.g., 10 mm or more). Alternatively, the ultrasound transducer 111 may not extend about the full rotational range of the window 73 of the sheath and/or the full longitudinal range of the window 73 of the sheath. In this arrangement, the window 73 may be configured to only partially expose the ultrasound transducer 111. Thus, a portion or amount of the ultrasound transducer 111 that is exposed to the tissue may be selected. This portion may have dimensions smaller than those of the window 73 if the window 73 is only partially disposed above the ultrasound transducer 111. Accordingly, the size of the lesion formed by the energy emitting region may be modulated.

It should be appreciated that while the ablation sources described herein are described as ultrasound energy sources, the invention is not limited in this respect. Although ultrasound energy is desirable because contact with tissue is not as critical as with other ablation energy sources, the ultrasound energy sources described could instead be implemented using radio frequency (RF) energy, microwave energy, direct current (DC), laser radiation, cryothermal energy, optical energy, or other energy forms to achieve tissue ablation.

Further, it should be appreciated that although the ultrasound assemblies and sheaths shown herein are capable of both longitudinal and rotational movement, each may be configured to be moveable in only one manner (e.g., longitudinally or circumferentially).

Figure 15:
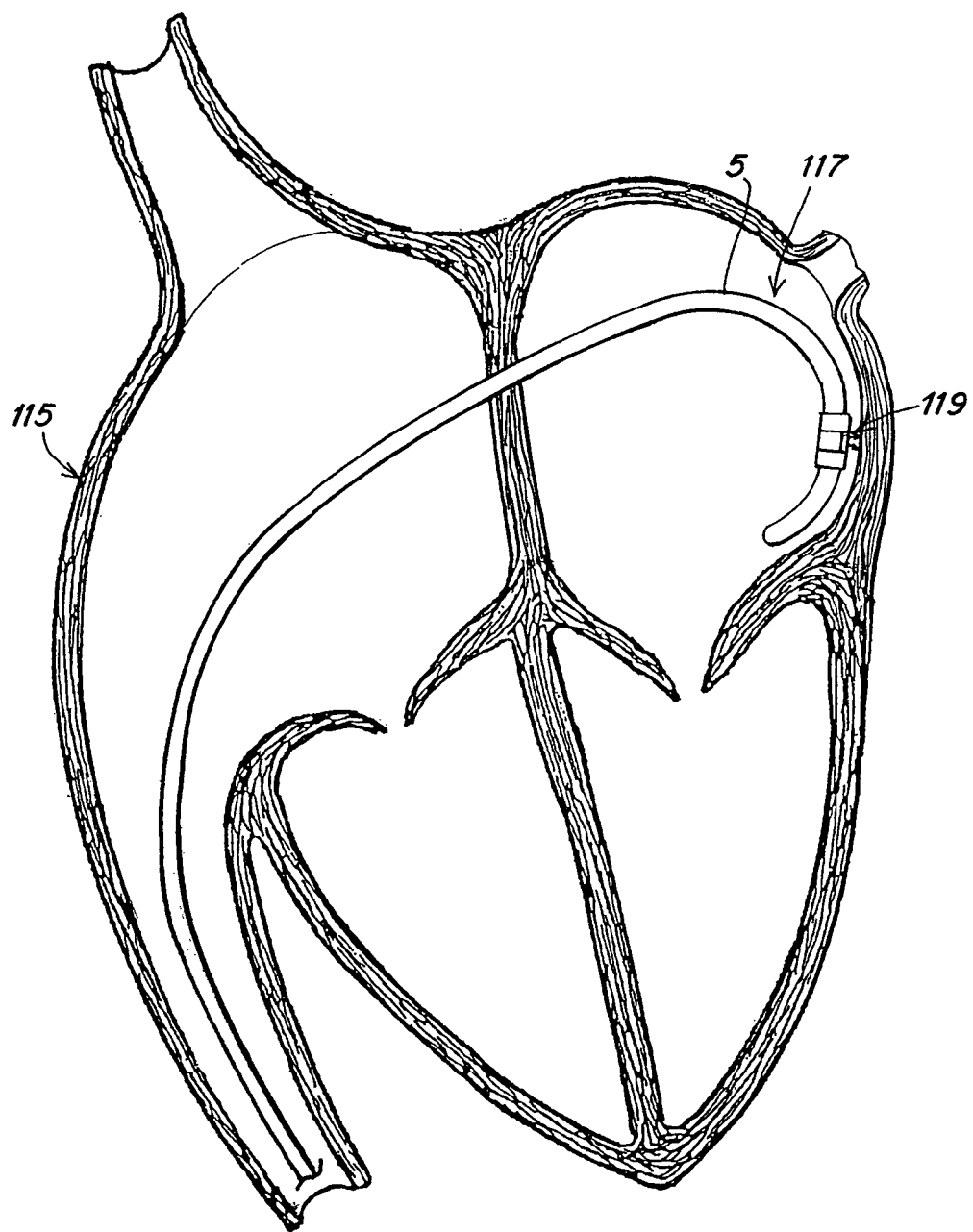
FIG. 15 illustrates a method of using the catheters described herein.

Reference is now made to FIG. 15, which illustrates how the catheters described herein may be used in endocardial applications. Catheter shaft 5 is introduced into a patient's heart 115. Imaging guidance (e.g., direct visual assessment, camera port, fluoroscopy, echocardiographic, magnetic resonance, etc.) may be used. FIG. 15 in particular illustrates catheter shaft 5 introduced into the left atrium of the patient's heart, although procedures may be performed in other chambers. Electrodes on the catheter 117 may be used to sense signals in the heart to determine a desired location for ablation.

Once at a desired location in the heart 115, the catheter 117 is configured so as to orient the ablation energy emitting region 119 in a desired configuration relative to the heart tissue. Energy is then applied to the adjacent tissue. Temperature sensors on the shaft may be used to monitor the temperature of the tissue during the ablation procedure. If a linear lesion is desired, the ablation energy emitting region 119 may be moved longitudinally along the catheter, while the shaft 5 remains relatively stationary. Sliding the ablation energy emitting region 119 in this manner may be easier and faster than repositioning a single "point" electrode since a complete linear lesion may be created in one application of RF energy. To determine whether a formed lesion is sufficient to cause a sufficient degree of conduction block, electrodes on the catheter 117 may be used to assess the lesion.

One or more lesions may be formed in the manner described above. The lesion(s) may be used to treat arrhythmias (e.g., atrial fibrillation) in the heart or other conditions.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A catheter comprising:
   a handle;
   a shaft coupled to the handle, the shaft having a central longitudinal axis; and
   an ultrasound assembly, coupled to the shaft, comprising first and second end portions and an ultrasound transducer disposed between the first and second end portions, wherein a radial distance from an outer surface of each of the first and second end portions to the central longitudinal axis is greater than a radial distance of an outer surface of the ultrasound transducer to the central longitudinal axis, and wherein the first and second end portions respectively comprise first and second temperature sensors and/or first and second electrodes and the entirety of the ultrasound transducer is disposed between the first and second temperature sensors and/or the first and second electrodes,
   wherein the first and second end portions rotate with respect to the shaft when the ultrasound transducer is rotated with respect to the shaft.

2. The catheter of claim 1, further comprising:
   at least one actuator coupled to the handle and the ultrasound assembly, the at least one actuator being adapted to move the ultrasound assembly relative to the shaft.

3. The catheter of claim 2, wherein the at least one actuator is further adapted to move the ultrasound assembly both longitudinally along the shaft and circumferentially about the shaft.

4. The catheter of claim 1, wherein the first and second end portions respectively comprise the first and second electrodes.

5. The catheter of claim 4, wherein the first and second electrodes are electrically independent.

6. The catheter of claim 1, wherein the first and second end portions respectively comprise the first and second temperature sensors.

7. The catheter of claim 1, further comprising an acoustic coupling medium disposed on the ultrasound transducer.

8. The catheter of claim 1, further comprising one or more irrigation ports positioned such that acoustic coupling fluid released therefrom is directed between the ultrasound transducer and adjacent tissue.

9. The catheter of claim 1, wherein the first and second end portions rotate with respect to the shaft when the ultrasound transducer is rotated with respect to the shaft such that the first and second temperature sensors and/or the first and second electrodes remain collinear with the ultrasound transducer as the ultrasound transducer is rotated.

10. The catheter of claim 1, wherein the catheter is configured to be used endocardially.

* * * * *